United States Patent
Haubs et al.

(10) Patent No.: US 9,499,512 B2
(45) Date of Patent: *Nov. 22, 2016

(54) PROCESS FOR PRODUCING A CYCLIC ACETAL IN A HETEROGENEOUS REACTION SYSTEM

(71) Applicant: Ticona GMBH, Sulzbach (Taunus) (DE)

(72) Inventors: Michael Haubs, Bad Kreuznach (DE); Damian Feord, Strasbourg (FR); (Continued)

(73) Assignee: Ticona GmbH, Sulzbach (Taunus) (DE)

( * ) Notice: Subject to any disclaimer, the term of this patent is extended or adjusted under 35 U.S.C. 154(b) by 53 days.

This patent is subject to a terminal disclaimer.

(21) Appl. No.: 14/359,594

(22) PCT Filed: Nov. 23, 2012

(86) PCT No.: PCT/EP2012/073543
§ 371 (c)(1),
(2) Date: May 21, 2014

(87) PCT Pub. No.: WO2013/076290
PCT Pub. Date: May 30, 2013

(65) Prior Publication Data
US 2014/0350216 A1  Nov. 27, 2014

(30) Foreign Application Priority Data

Nov. 24, 2011  (EP) .................................. 11190567
Nov. 24, 2011  (EP) .................................. 11190574
Nov. 24, 2011  (EP) .................................. 11190586

(51) Int. Cl.
*C08G 59/00* (2006.01)
*C07D 323/06* (2006.01)
(Continued)

(52) U.S. Cl.
CPC ............. *C07D 323/06* (2013.01); *C07C 47/04* (2013.01); *C07D 323/04* (2013.01); *C08G 2/10* (2013.01);
(Continued)

(58) Field of Classification Search
CPC ................... C07D 323/06; C08G 2/10; C08G 65/06; C08G 65/16
(Continued)

(56) References Cited

U.S. PATENT DOCUMENTS 3,305,529 A  2/1967  Reynolds et al.
3,457,227 A  7/1969  Kennedy
(Continued)

FOREIGN PATENT DOCUMENTS

AT  252913  3/1967
CN  101665409  3/2010
(Continued)

OTHER PUBLICATIONS

International Search Report and Written Opinion for application PCT/EP2012/073543 dated Jan. 2, 2013.
(Continued)

*Primary Examiner* — Shane Fang
(74) *Attorney, Agent, or Firm* — Dority & Manning, P.A.

(57) ABSTRACT

A process for producing a cyclic acetal is disclosed. According to the process, a formaldehyde source is combined with an aprotic compound and contacted with a heterogeneous catalyst which causes the formaldehyde source to convert into a cyclic acetal such as trioxane. The catalyst, for instance, may comprise a solid catalyst such as an ion exchange resin. In one embodiment, the process is used for converting anhydrous formaldehyde gas to trioxane. The anhydrous formaldehyde gas may be produced form an aqueous formaldehyde solution by an extractive distillation.

24 Claims, 2 Drawing Sheets

(72) Inventors: Joni Sianturi, Sulzbach (DE); Klaus Kurz, Kelsterbach (DE); Jurgen Lingnau, Mainz-Laubenheim (DE)

(51) Int. Cl.

| | |
|---|---|
| *C08G 2/10* | (2006.01) |
| *C08G 2/36* | (2006.01) |
| *C07C 47/04* | (2006.01) |
| *C08G 65/30* | (2006.01) |
| *C07D 323/04* | (2006.01) |
| *C08G 65/16* | (2006.01) |
| *C08G 65/06* | (2006.01) |

(52) U.S. Cl.
CPC ............... *C08G 2/36* (2013.01); *C08G 65/06* (2013.01); *C08G 65/16* (2013.01); *C08G 65/30* (2013.01); *C08G 2650/62* (2013.01); *Y02P 20/125* (2015.11)

(58) Field of Classification Search
USPC ........................................................ 528/403
See application file for complete search history.

(56) References Cited

U.S. PATENT DOCUMENTS

| | | | |
|---|---|---|---|
| 3,471,998 A | 10/1969 | Ishida et al. | |
| 3,506,615 A | 4/1970 | Chen | |
| 3,697,546 A | 10/1972 | Asakawa et al. | |
| 3,804,808 A | 4/1974 | Ishii et al. | |
| 4,323,502 A | 4/1982 | Muck et al. | |
| 4,330,474 A | 5/1982 | Nehring | |
| 4,358,623 A | 11/1982 | Murphy et al. | |
| 4,420,641 A | 12/1983 | Gerberich et al. | |
| 4,450,301 A | 5/1984 | McMillan et al. | |
| 4,563,536 A | 1/1986 | Yoshida et al. | |
| 4,962,235 A | 10/1990 | Morishita et al. | |
| 4,967,014 A | 10/1990 | Masamoto et al. | |
| 5,008,463 A | 4/1991 | Beck et al. | |
| 5,508,448 A | 4/1996 | Emig et al. | |
| 5,767,294 A | 6/1998 | Steele et al. | |
| 5,929,257 A * | 7/1999 | Kashihara | C07D 323/06 549/368 |
| 6,232,507 B1 | 5/2001 | Kaiser et al. | |
| 6,313,323 B1 * | 11/2001 | Werner | B01J 27/16 549/368 |
| 6,362,305 B1 | 3/2002 | Schweers et al. | |
| 6,388,102 B2 | 5/2002 | Schweers et al. | |
| 6,448,448 B1 | 9/2002 | Schweers et al. | |
| 6,472,566 B2 | 10/2002 | Schweers et al. | |
| 6,653,487 B2 | 11/2003 | Schweers et al. | |
| 6,781,018 B2 | 8/2004 | Liu et al. | |
| 7,301,055 B2 | 11/2007 | Hoffmockel et al. | |
| 7,390,932 B2 | 6/2008 | Stroefer et al. | |
| 7,598,402 B2 | 10/2009 | Chen et al. | |
| 2006/0058537 A1 | 3/2006 | Haubs et al. | |
| 2006/0185513 A1 | 8/2006 | Stroefer et al. | |
| 2008/0234459 A1 | 9/2008 | Lang et al. | |
| 2010/0004409 A1 | 1/2010 | Schwittay et al. | |
| 2010/0121081 A1 | 5/2010 | Lang et al. | |
| 2010/0145079 A1 | 6/2010 | Stroefer et al. | |

FOREIGN PATENT DOCUMENTS

| | | |
|---|---|---|
| DE | 4137846 | 5/1993 |
| DE | 19822598 | 11/1999 |
| GB | 1012372 | 12/1965 |
| GB | 1130513 | 10/1968 |
| GB | 1524440 | 9/1978 |

OTHER PUBLICATIONS

Yamaguchi T. et al: "Synthesis of cyclooligomers of formaldehyde in liquid sulfur dioxide", Chemistry and Industry, vol. 43, Oct. 23, 1971 pp. 1226-1227. XP008149518, Society of Chemical Industry, London; GB ,ISSN: 0009-3068.
Shoujin Su, Philippe Zaza and Albert Renken: Catalytic Dehydrogenation of Methanol to Water-Free Formaldehyde, Chem. Eng. Technol. 17 (1994) pp. 34-40.
Co pending U.S. Appl. No. 14/359,223, filed May 19, 2014.
Co pending U.S. Appl. No. 14/359,203, filed May 19, 2014.
Co pending U.S. Appl. No. 14/359,319, filed May 20, 2014.
Co pending U.S. Appl. No. 14/359,308, filed May 20, 2014.
Co pending U.S. Appl. No. 14/359,314, filed May 20, 2014.
Co pending U.S. Appl. No. 14/359,333, filed May 20, 2014.
New Jersey Department of Health and Senior Services, Hazardous Substance Fact Sheet. "Boron Trifluoride Diethy Etherate." (c) Apr. 2000. Available from : < http://nj.gov/health/eoh/rtkweb/documents/fs/0248.pdf>.
Abstract of Japanese Patent—JPH06228126, Aug. 16, 1994, 1 page.
Abstract of Japanese Patent JP2007230979, Sep. 13, 2007, 2 pages.
JP S47-007029 B.
JP S46-031867 B.
JP S37-011033 B.

* cited by examiner

PROCESS FOR PRODUCING A CYCLIC ACETAL IN A HETEROGENEOUS REACTION SYSTEM

RELATED APPLICATIONS

This present application claims priority to PCT International Patent Application No. PCT/EP2012/073543 having a filing date of Nov. 23, 2012, and which claims filing benefit to European Patent Application No. 11190567.5 filed on Nov. 24, 2011, European Patent Application No. 11190574.1 filed on Nov. 24, 2011, and European Patent Application No. 11190586.5 filed on Nov. 24, 2011 which are all hereby incorporated by reference in their entirety.

BACKGROUND 1,3,5-Trioxane (hereinafter "trioxane") is the cyclic trimer of formaldehyde. Trioxane is mainly used as a starting material for the manufacturing of polyoxymethylenes (POM) which is a high performance polymer having desirable and exceptional properties in terms of mechanical, chemical and temperature stability. Polyoxymethylene polymers are available as homo- and copolymers.

As the polyoxymethylene market is growing, there is a desire on the side of the trioxane producers to expand their production capacities in order to satisfy the trioxane demand on a competitive basis. The major technical process for the production of trioxane is the conversion of aqueous formaldehyde solutions in the presence of concentrated sulfuric acid as a catalyst. The process for the production of trioxane known in the prior art is complex and comprises an extraction step which necessitates tedious solvent recovery steps. Furthermore, the process conventionally and commercially known in the prior art is time and energy consuming and leads to a low degree of conversion of the formaldehyde source into the desired cyclic acetals. Furthermore, the amount of side products formed by the process is high.

In view of the above, a need currently exists for an efficient process for producing cyclic acetals, such as trioxane. A need also exists for a process for producing cyclic acetals that has a relatively high conversion rate. A need also exists for a process for producing cyclic acetals from different formaldehyde sources.

SUMMARY

In general, the present disclosure is directed to a process for producing one or more cyclic acetals from a formaldehyde source. The formaldehyde source may comprise gaseous formaldehyde, paraformaldehyde, polyoxymethylene homo- and copolymers, mixtures containing formaldehyde such as formaldehyde and trioxane mixtures, and blends thereof. The formaldehyde source is combined with an aprotic compound and contacted with a catalyst. In accordance with the present disclosure, the catalyst is a heterogeneous catalyst. For instance, the catalyst may comprise a solid catalyst, such as an ion exchange material.

The aprotic compound may be polar. For instance, in one embodiment, the aprotic compound may be dipolar. In one embodiment, the aprotic compound comprises a sulfur containing organic compound such as a sulfoxide, a sulfone, a sulfonate ester, or mixtures thereof. In one embodiment, the aprotic compound comprises sulfolane.

The aprotic compound may also have a relatively high static permittivity or dielectric constant of greater than about 15. The aprotic compound may also be nitro-group free. In particular, compounds having nitro-groups may form undesired side reactions within the process.

Once the cyclic acetal is formed from the formaldehyde source, the cyclic acetal can be easily separated from the aprotic compound and the catalyst. In one embodiment, for instance, the cyclic acetal may be separated by distillation from the aprotic compound which may have a much higher boiling point than the cyclic acetal. The aprotic compound, for instance, may have a boiling point of greater than about 120° C., such as greater than about 140° C., such as greater than about 160° C., such as even greater than about 180° C. at a pressure of one bar. Preferably, the aprotic compound does not form an azeotrope with the cyclic acetal.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures in which.

Figure 1:
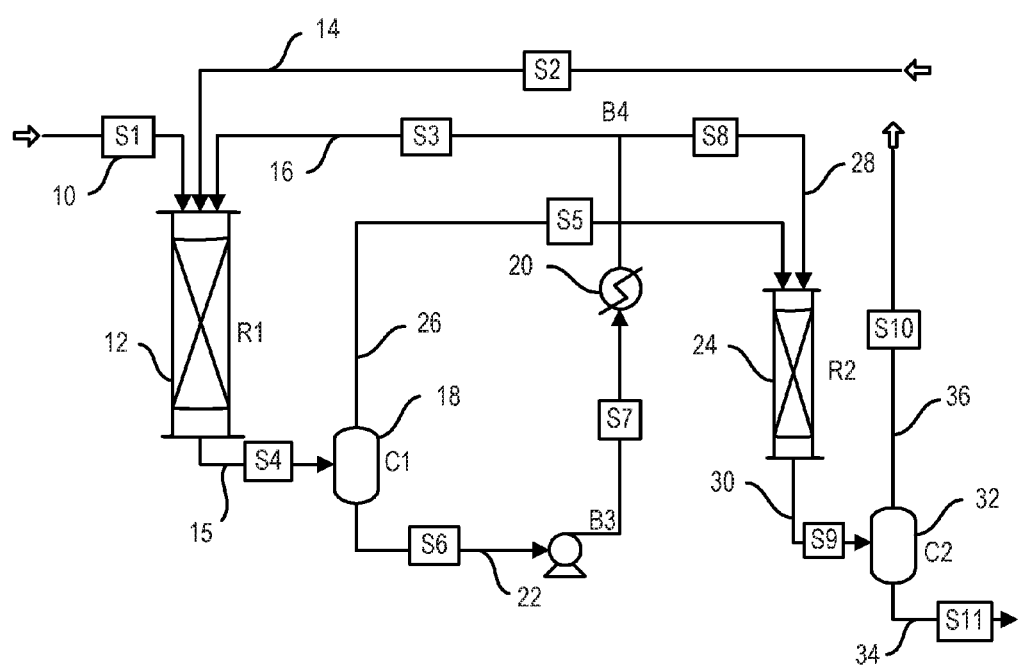
FIG. 1 is a schematic diagram of one embodiment of a process in accordance with the present disclosure.

Repeat use of reference characters in the present specification and drawings is intended to represent same or analogous features or elements of the present disclosure.

DETAILED DESCRIPTION

The present disclosure is generally directed to a process for producing a cyclic acetal. Of particular advantage, cyclic acetals can be produced from all different types of formaldehyde sources. As used herein, a formaldehyde source includes formaldehyde and oligomers or polymers formed from formaldehyde. Thus, a formaldehyde source can include paraformaldehyde, oxymethylene homopolymers, and oxymethylene copolymers.

The formaldehyde source is contacted with a catalyst in the presence of an aprotic compound to form a cyclic acetal. The aprotic compound facilitates production of the cyclic acetal in a manner that greatly enhances the conversion rates. Of particular advantage, the cyclic acetal produced according to the process can then be easily separated from the aprotic compound. For instance, in one embodiment, the cyclic acetal can be separated or isolated from the aprotic compound through a simple distillation process, since the aprotic compound may have a much higher boiling point than the cyclic acetal.

In accordance with the present disclosure, the catalyst that is used during conversion of the formaldehyde into the cyclic acetal comprises a heterogeneous catalyst. The catalyst, for instance, can be immiscible in the aprotic compound and the formaldehyde source. In one embodiment, the catalyst comprises a solid catalyst. As used herein, a solid catalyst is a catalyst that includes at least one solid component. For instance, a catalyst may comprise an acid that is adsorbed or otherwise fixed to a solid support. The catalyst may also be present in liquid phase which is not miscible or is at least partially immiscible with the aprotic compound.

Various advantages and benefits are obtained when using a heterogeneous catalyst. For example, when using a heterogeneous catalyst, the catalyst can be easily separated from the aprotic compound, the formaldehyde source, and/or the cyclic acetal that is produced. In addition, in one embodiment a solid catalyst is used that remains in the reactor that is used to produce the cyclic acetal. In this manner, the catalyst can be used over and over again during the process.

Furthermore solid catalysts tend to be less corrosive to their environments e.g vessel walls.

Through the process of the present disclosure, a formaldehyde source may be converted into one or more cyclic acetals at extremely fast reaction times, such as within minutes. In addition, very high conversion rates can be achieved. For instance, in one embodiment, a majority of the formaldehyde source may be converted into one or more cyclic acetals.

In one embodiment, the aprotic compound is a liquid when contacted with the formaldehyde source. The formaldehyde source, on the other hand, may comprise gaseous formaldehyde, a liquid, or a solid. The formaldehyde source may dissolve into the aprotic compound or may be absorbed by the aprotic compound to form a homogeneous phase. The aprotic compound and the catalyst, in one embodiment, may comprise a liquid reaction mixture or a liquid medium.

The formaldehyde source reacts (converts) in the presence of the catalyst.

Cyclic acetals within the meaning of the present disclosure relate to cyclic acetals derived from formaldehyde. Typical representatives are represented the following formula:

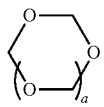

wherein a is an integer ranging from 1 to 3.

Preferably, the cyclic acetals produced by the process of the present disclosure are trioxane (a=1) and/or tetroxane (a=2). Trioxane and tetroxane usually form the major part (at least 80 wt.-%, preferably at least 90 wt.-%) of the cyclic acetals formed by the process of the present disclosure.

The weight ratio of trioxane to tetroxane varies with the heterogeneous catalyst used. Typically, the weight ratio of trioxane to tetroxane ranges from about 3:1 to about 40:1, preferably about 4:1 to about 20:1.

The process of the invention is carried out in the presence of a heterogeneous catalyst for the conversion of the formaldehyde source into cyclic acetals. Suitable catalysts are any components which accelerate the conversion of the formaldehyde source to the cyclic acetals. The catalyst is a catalyst for the conversion (reaction) of a formaldehyde source into cyclic acetals, preferably into trioxane and/or tetroxane.

Usually, cationic catalysts can be used for the process of the invention. The catalysts can be a solid catalyst or an immiscible liquid catalyst. A typical liquid immiscible catalyst is a liquid acidic ion exchange resin. Solid catalyst means that the catalyst is at least partly, preferably completely in solid form under the reaction conditions. Typical solid catalysts which may be used for the process of the present invention are acid ion-exchange material, strongly acidic ion-exchange material, Lewis acids and/or Broensted acids fixed on a solid support, wherein the support may be an inorganic material such as $SiO_2$ or organic material such as organic polymers.

Preferred catalysts that may be fixed to a solid support are selected from the group consisting of Broensted acids and Lewis acids. The catalyst can be selected from the group consisting of trifluoroalkanesulfonic acids such as trifluoromethanesulfonic acid, perchloric acid, methanesulfonic acid, toluenesulfonic acid and sulfuric acid, or derivatives thereof such as anhydrides or esters or any other derivatives that generate the corresponding acid under the reaction conditions. Lewis acids like boron trifluoride, arsenic pentafluoride can also be used. Heteropolyacides such as tungsten heteropoly acides (e.g. tungstophosphates) may also be used. It is also possible to use mixtures of all the individual catalysts mentioned above.

In one embodiment, the heterogeneous catalyst may comprise a Lewis or Broensted acid species dissolved in an inorganic molten salt. The molten salt may have a melting point below 200° C., such as less than about 100° C., such as less than about 30° C. The molten salt can then be immobilized or fixed onto a solid support as described above. The solid support, for instance, may be a polymer or a solid oxide. An example of an organic molten salt include ionic liquids. For instance, the ionic liquid may comprise 1-n-alkyl-3-methylimidazolium triflate. Another example is 1-n-alkyl-3-methylimidazolium chloride.

In one embodiment, the acidic compound present in the catalyst can have a pKa below 0, such as below about −1, such as below about −2, when measured in water at a temperature of 18° C. The pKa number expresses the strength of an acid and is related to the dissociation constant for the acid in an aqueous solution.

Examples of heterogeneous catalysts that may be used according to the present disclosure include the following:

(1) solid catalysts represented by acidic metal oxide combinations which can be supported onto usual carrier materials such as silica, carbon, silica-alumina combinations or alumina. These metal oxide combinations can be used as such or with inorganic or organic acid doping. Suitable examples of this class of catalysts are amorphous silica-alumina, acid clays, such as smectites, inorganic or organic acid treated clays, pillared clays, zeolites, usually in their protonic form, and metal oxides such as $ZrO_2$—$TiO_2$ in about 1:1 molar combination and sulfated metal oxides e.g. sulfated $ZrO_2$. Other suitable examples of metal oxide combinations, expressed in molar ratios, are: $TiO_2$—$SiO_2$ 1:1 ratio; and $ZrO_2$—$SiO_2$ 1:1 ratio.

(2) several types of cation exchange resins can be used as acid catalyst to carry out the reaction. Most commonly, such resins comprise copolymers of styrene, ethylvinyl benzene and divinyl benzene functionalized so as to graft $SO_3H$ groups onto the aromatic groups. These acidic resins can be used in different physical configurations such as in gel form, in a macro-reticulated configuration or supported onto a carrier material such as silica or carbon or carbon nanotubes. Other types of resins include perfluorinated resins carrying carboxylic or sulfonic acid groups or both carboxylic and sulfonic acid groups. Known examples of such resins are: NAFION™, and AMBERLYST resins. The fluorinated resins can be used as such or supported onto an inert material like silica or carbon or carbon nanotubes entrapped in a highly dispersed network of metal oxides and/or silica.

(3) heterogeneous solids, having usually a lone pair of electrons, like silica, silica-alumina combinations, alumina, zeolites, silica, activated charcoal, sand and/or silica gel can be used as support for a Broensted acid catalyst, like methane sulfonic acid or para-toluene sulfonic acid, or for a compound having a Lewis acid site, such as SbF$_5$, to thus interact and yield strong Broensted acidity. Heterogeneous solids, like zeolites, silica, or mesoporous silica or polymers like e.g. polysiloxanes can be functionalized by chemical grafting with a Broensted acid group or a precursor therefore to thus yield acidic groups like sulfonic and/or carboxylic acids or precursors therefore. The functionalization can be introduced in various ways known in the art like: direct grafting on the solid by e.g. reaction of the SiOH groups of the silica with chlorosulfonic acid; or can be attached to the solid by means of organic spacers which can be e.g. a perfluoro alkyl silane derivative. Broensted acid functionalized silica can also be prepared via a sol gel process, leading to e.g. a thiol functionalized silica, by co-condensation of Si(OR)$_4$ and e.g. 3-mercaptopropyl-tri-methoxy silane using either neutral or ionic templating methods with subsequent oxidation of the thiol to the corresponding sulfonic acid by e.g. H$_2$O$_2$. The functionalized solids can be used as is, i.e. in powder form, in the form of a zeolitic membrane, or in many other ways like in admixture with other polymers in membranes or in the form of solid extrudates or in a coating of e.g. a structural inorganic support e.g. monoliths of cordierite; and (4) heterogeneous heteropolyacids having most commonly the formula H$_x$PM$_y$O$_z$. In this formula, P stands for a central atom, typically silicon or phosphorus. Peripheral atoms surround the central atom generally in a symmetrical manner. The most common peripheral elements, M, are usually Mo or W although V, Nb, and Ta are also suitable for that purpose. The indices xyz quantify, in a known manner, the atomic proportions in the molecule and can be determined routinely. These polyacids are found, as is well known, in many crystal forms but the most common crystal form for the heterogeneous species is called the Keggin structure. Such heteropolyacids exhibit high thermal stability and are non-corrosive. The heterogeneous heteropolyacids are preferably used on supports selected from silica gel, kieselguhr, carbon, carbon nanotubes and ion-exchange resins. A preferred heterogeneous heteropolyacid herein can be represented by the formula H$_3$PM$_{12}$O$_{40}$ wherein M stands for W and/or Mo. Examples of preferred PM moieties can be represented by PW$_{12}$, PMo$_{12}$, PW$_{12}$/SiO$_2$, PW$_{12}$/carbon and SiW$_{12}$.

As described above, formaldehyde or a formaldehyde source is converted to a cyclic acetal by contacting the formaldehyde source with aprotic compound and a catalyst. The formaldehyde source, for instance, may comprise gaseous formaldehyde. Gaseous formaldehyde can have a water content of less than about 5 wt-%, such as less than about 2 wt-%, such as less than about 1 wt-%, such as less that about 0.5 wt-%. In an alternative embodiment, the formaldehyde source may comprise paraformaldehyde, which can have a water content of less than 5 wt-%, such as less than 2 wt-%, such as less than about 1 wt-%.

In still another embodiment, the formaldehyde source may comprise a polyoxymethylene homo- or copolymer. The polyoxymethylene polymer can have a molecular weight of generally greater than about 2000 Dalton. A gas or liquid stream may be fed to the reactor that contains formaldehyde in combination with other components. For instance, the formaldehyde may be present with trioxane, or other monomers used to produce polyoxymethylene polymers. In yet another embodiment, the formaldehyde source may comprise an aqueous formaldehyde solution. The aqueous formaldehyde solution, for instance, may contain water in amounts greater than about 30%, such as in amounts greater than about 50%, such as in amounts from about 40% to about 70%.

As used herein, an aprotic compound is a compound that does not contain any substantial amounts of hydrogen atoms which can disassociate. In one embodiment, the aprotic compound is liquid under the reaction conditions. Therefore, the aprotic compound may have a melting point of about 180° C. or less, preferably about 150° C. or less, more preferably about 120° C. or less, especially about 60° C. or less.

For practical reasons, it is advantageous to use an aprotic compound which has a melting point in the order of preference (the lower the melting point the more preferred) of below about 50° C., below about 40° C. and below about 30° C. and below about 20° C. Especially, aprotic compounds which are liquid at about 25 or about 30° C. are suitable since they can be easily transported by pumps within the production plant.

Further, the aprotic compound may have a boiling point of about 120° C. or higher, preferably about 140° C. or higher, more preferably about 160° C. or higher, especially about 180° C. or higher, determined at 1 bar. In a further embodiment the boiling point of the aprotic compound is about 200° C. or higher, preferably about 230° C. or higher, more preferably about 240° C. or higher, further preferably about 250° C. or higher and especially about 260° C. or higher or 270° C. or higher. The higher the boiling point the better the cyclic acetals, especially trioxane and/or tetroxane, formed by the process of the present disclosure can be separated by distillation. Therefore, according to an especially preferred embodiment of the present disclosure the boiling point of the aprotic compound is at least about 20° C. higher than the boiling point of the cyclic acetal formed, in particular at least about 20° C. higher than the boiling point of trioxane and/or tetroxane.

Additionally, aprotic compounds are preferred which do not form an azeotrope with the cyclic acetal, especially do not form an azeotrope with trioxane.

In a preferred embodiment of the present invention the reaction mixture or liquid medium in the reactor 40 comprises at least about 20 wt.-%, preferably at least about 40 wt.-%, more preferably at least about 60 wt.-%, most preferably at least about 80 wt.-% and especially at least about 90 wt.-% of the aprotic compound(s), wherein the weight is based on the total weight of the reaction mixture. The liquid medium or the reaction mixture or the liquid mixture (A) may comprise one or more aprotic compound(s).

In a preferred embodiment the liquid medium is essentially consisting of the aprotic compound. Essentially consisting of means that the liquid medium comprises at least about 95 wt.-%, preferably at least about 98 wt.-%, more preferably at least about 99 wt.-%, especially at least about 99.5 wt.-%, in particular at least about 99.9 wt.-% of the aprotic compound(s). In a further embodiment of the invention the liquid medium is the aprotic compound, i.e., the liquid medium is consisting of the aprotic compound.

It has been found that liquid aprotic compounds which at least partly dissolve or absorb the formaldehyde source lead to excellent results in terms of conversion of the formaldehyde source into the desired cyclic acetals.

Therefore, aprotic compounds are preferred which at least partly dissolve or absorb the formaldehyde source under the reaction conditions. Preferred are aprotic compounds which dissolve paraformaldehyde (98 wt.-% formaldehyde, 2 wt.-% water) [can also be expressed as Pn=moles of formaldehyde/moles of water=(98/30)/(2/18)=approx. 29] at the reaction temperature in an amount of at least about 0.1 wt.-%, wherein the weight is based on the total weight of the solution.

The aprotic compound used in the process can be a polar aprotic compound, especially a dipolar compound. Polar aprotic solvents are much more suitable to dissolve the formaldehyde source. Non-polar aprotic compounds such as unsubstituted hydrocarbons (e.g. cyclic hydrocarbons such as cyclohexane, or alicyclic hydrocarbons such as hexane, octane, decane, etc.) or unsubstituted unsaturated hydrocarbons or unsubstituted aromatic compounds are less suitable. Therefore, according to a preferred embodiment the aprotic compound is not an unsubstituted hydrocarbon or unsubstituted unsaturated hydrocarbon or unsubstituted aromatic compound. Further, preferably the reaction mixture comprises unsubstituted hydrocarbons and/or unsubstituted unsaturated hydrocarbons and/or unsubstituted aromatic compounds in an amount of less than about 50 wt.-%, more preferably less than about 25 wt.-%, further preferably less than about 10 wt.-%, especially less than about 5 wt.-%, e.g. less than about 1 wt.-% or about 0 wt.-%.

Halogen containing compounds are less preferred due to environmental aspects and due to their limited capability to dissolve the formaldehyde sources. Further, the halogenated aliphatic compounds may cause corrosions in vessels or pipes of the plant and it is difficult to separate the cyclic acetals formed from the halogenated compounds.

According to one embodiment, the aprotic compound is halogen free. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or less than 50 ppm of halogenated compounds.

Likewise, the use of (liquid) sulphur dioxide leads to difficulties with isolation of the cyclic acetals. Therefore, the aprotic compound is preferably free of sulphur dioxide. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or 0 wt.-% of sulphur dioxide.

Polar aprotic compounds are especially preferred. According to a preferred embodiment of the invention the aprotic compound has a relative static permittivity of more than about 15, preferably more than about 16 or more than about 17, further preferably more than about 20, more preferably of more than about 25, especially of more than about 30, determined at 25° C. or in case the aprotic compound has a melting point higher than 25° C. the relative permittivity is determined at the melting point of the aprotic compound.

The relative static permittivity, $\varepsilon_r$, can be measured for static electric fields as follows: first the capacitance of a test capacitor $C_0$, is measured with vacuum between its plates. Then, using the same capacitor and distance between its plates the capacitance $C_x$ with an aprotic compound between the plates is measured. The relative dielectric constant can be then calculated as $$\varepsilon_r = \frac{C_x}{C_0}.$$

Within the meaning of the present invention the relative permittivity is determined at 25° C. or in case the aprotic compound has a melting point higher than 25° C. the relative permittivity is determined at the melting point of the aprotic compound.

According to a further aspect of the invention the aprotic compound is a dipolar aprotic compound.

The aprotic compound within the meaning of the present invention is generally a dipolar and non-protogenic compound which has a relative permittivity as defined above of more than 15, preferably more than 25 or more than 30, determined at 25° C. or in case the aprotic compound has a melting point higher than 25° C. the relative permittivity is determined at the melting point of the aprotic compound.

The process can be carried out in manner wherein the formaldehyde source is completely dissolved or absorbed in the liquid medium or reaction mixture or liquid mixture (A).

Therefore, according to one embodiment the formaldehyde source and the aprotic compound form a homogenous phase under the reaction conditions. Suitable aprotic compounds are selected from the group consisting of organic sulfoxides, organic sulfones, organic sulfonate ester, and mixtures thereof.

According to a preferred embodiment the aprotic compound is selected from sulfur containing organic compounds.

Further, the aprotic compound is preferably selected from the group consisting of cyclic or alicyclic organic sulfoxides, alicyclic or cyclic sulfones, and mixtures thereof. Excellent results can be achieved by aprotic compounds as represented by the following formula (I):

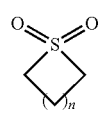

(I)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched. Preferred compounds of formula (I) are sulfolane, methylsulfolane, dimethylsulfolane, ethylsulfolane, diethylsulfolane, propylsulfolane, dipropylsulfolane, butylsulfolane, dibutylsulfolane, pentylsulfolane, dipentylsulfolane, and hexylsulfolane as well as octylsulfolane.

According to the most preferred embodiment the aprotic compound is sulfolane (tetrahydrothiophene-1,1-dioxide).

Sulfolane is an excellent solvent for the formaldehyde source, it is stable under acidic conditions, it does not deactivate the catalysts and it does not form an azeotrope with trioxane. Further, it is a solvent which is inert under the reaction conditions.

Unless indicated otherwise the expression "reaction mixture" refers to the mixture which is used for the reaction of the formaldehyde source to the cyclic acetals. The concentrations and amounts of the individual components of the reaction mixture refer to the concentrations and amounts at the beginning of the reaction. In other words the reaction mixture is defined by the amounts of its starting materials, i.e. the amounts of initial components.

Likewise the amounts defined for the "liquid mixture" refer to the amounts of the components at the beginning of the reaction, i.e. prior to the reaction.

The formaldehyde source reacts to the cyclic acetals and, as a consequence, the concentration of the formaldehyde source decreases while the concentration of the cyclic acetals increases.

At the beginning of the reaction a typical reaction mixture of the invention comprises a formaldehyde source which is at least partly, preferably completely dissolved or absorbed in sulfolane.

Further, an especially preferred embodiment of the present invention is a process for producing cyclic acetal comprising reacting a formaldehyde source in the presence of a catalyst wherein the reaction is carried out in sulfolane or a process for producing cyclic acetals from a formaldehyde source in the presence of a catalyst and sulfolane.

A further preferred aprotic compound is represented by formula (II):

(II)

wherein $R^1$ and $R^2$ are independently selected from $C_1$-$C_8$-alkyl which may be branched or unbranched, preferably wherein $R^1$ and $R^2$ independently represent methyl or ethyl. Especially preferred is dimethyl sulfone.

According to a further preferred embodiment the aprotic compound is represented by formula (III):

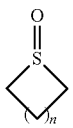

(III)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched.

Suitable aprotic compounds are also represented by formula (IV):

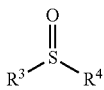

(IV)

wherein $R^3$ and $R^4$ are independently selected from $C_1$-$C_8$-alkyl which may be branched or unbranched, preferably wherein $R^1$ and $R^2$ independently represent methyl or ethyl.

Especially preferred is dimethyl sulfoxide.

Suitable aprotic compounds may be selected from aliphatic dinitriles, preferably adiponitrile.

In a further aspect of the invention a mixture of two or more aprotic compounds is used. A mixture of aprotic compounds may be used to decrease the melting point of the aprotic medium. In a preferred embodiment the aprotic compound comprises or is consisting of a mixture of sulfolane and dimethyl sulfoxide.

Advantageously, the aprotic compound does not essentially deactivate the catalyst. Preferably, under the reaction conditions the aprotic compound does essentially not deactivate the catalyst used in the process of the present invention. Aprotic solvents such as dimethylformamide (DMF), dimethylacetamide (DMAC) or N-methylpyrrolidone (NMP) are too basic and therefore may deactivate the catalyst and, as a consequence, said solvents are less suitable. According to a preferred embodiment of the present invention the liquid reaction mixture is essentially free of amides, preferably essentially free of acylic or cyclic amides. Essentially free means that the amides may be present in an amount of less than about 5 wt.-%, preferably less than about 2 wt.-%, more preferably less than 0.5 wt.-%, especially less than about 0.01 wt.-% and, in particular, less than 0.001 wt.-% or about 0 wt.-%, wherein the weight is based on the total weight of the liquid reaction mixture.

Nitro group containing compounds can lead to undesired side products or even demonstrate an insufficient solubility for the formaldehyde sources.

Therefore, the aprotic compound preferably does not comprise a nitro group and/or a nitrogen atom. Further, according to a preferred embodiment of the present invention the aprotic compound is a non-aromatic aprotic compound. Especially, the aprotic compound is not nitrobenzene or an aromatic nitro compound. Further, preferably, the aprotic compound does not comprise ether.

Within the meaning of the present invention the aprotic compound does not deactivate the catalyst if under the reaction conditions less than about 95%, preferably less than about 50%, more preferably less than about 10%, of the Broensted acid catalyst used protonates the aprotic compound. In case a Lewis acid catalyst is used the aprotic compound does not deactivate the catalyst if under the reaction conditions less than about 90 wt-%, preferably less than about 50 wt.-%, more preferably less than about 10 wt-% of the Lewis acid catalyst forms a complex with the aprotic compound.

The degree of protonation and complex formation can be determined by NMR spectroscopy such as $^1$H or $^{13}$C-NMR. The degree of protonation and complex formation is determined at 250° C., preferably in $d_6$-DMSO.

The deactivation of the catalyst can also be determined in the following manner:

10 g of commercially available paraformaldehyde (95 wt-%) is dissolved in 100 g of sulfolane at a temperature sufficient to dissolve the paraformaldehyde in such a way that no gaseous formaldehyde can escape. The clear solution is kept at 90° C. and 0.1 wt-% of triflic acid is added. The rate of the formation of trioxane is measured (by measuring the concentration of trioxane as a function of time).

The same experiment is repeated, except that 10 g of the sulfolane are replaced by 10 g of the aprotic compound to be tested. If the rate of trioxane formation is still greater than about 1%, preferably greater than about 5%, more preferably greater than about 10%, of the rate of the initial experiment then it is concluded that the aprotic compound in question does not deactivate the catalyst (even though it may reduce its activity).

The aprotic compound should not be too basic in order to avoid deactivation of the catalysts. On the other hand the aprotic compound preferably does not chemically react with the formaldehyde source under the reaction conditions, i.e. is an inert aprotic compound.

Preferably, under the reaction conditions the aprotic compound should not react chemically with the formaldehyde source or the cyclic acetal obtained by the process of the invention. Compounds like water and alcohols are not suitable as they react with formaldehyde. Within the meaning of the present invention an aprotic compound does not chemically react with the formaldehyde source when it meets the following test criteria:

5 g of commercially available paraformaldehyde (95 wt.-%) is added to 100 g of the aprotic compound containing 0.1 wt.-% trifluoromethanesulfonic acid and heated at 120° C. for 1 hour with stirring in a closed vessel so that no gaseous formaldehyde can escape. If less than about 1 wt.-%, preferably less than about 0.5 wt.-%, more preferably less than about 0.1 wt.-% and most preferably less than about 0.01 wt.-% of the aprotic compound has chemically reacted, then the aprotic compound is considered not to have reacted with the formaldehyde source. If the aprotic compound meets the criteria it is considered inert.

Further, under the acidic reaction conditions the aprotic compound should be essentially stable. Therefore, aliphatic ethers or acetals are less suitable as aprotic compounds. The aprotic compound is considered stable under acidic conditions within the meaning of the present invention if the aprotic compound meets the following test conditions:

100 g of the aprotic compound to be tested containing 0.5% by weight (wt.-%) trifluoromethanesulfonic acid is heated at 120° C. for 1 hour. If less than about 0.5 wt.-%, preferably less than about 0.05 wt.-%, more preferably less than about 0.01 wt.-% and most preferably less than about 0.001 wt.-% of the aprotic compound has chemically reacted, then the aprotic compound is considered to be stable under acidic conditions.

The process of the invention can also be used to change the ratio of cyclic acetals derived from formaldehyde. Therefore, the formaldehyde source can also comprise cyclic acetals selected from the group consisting of trioxane, tetroxane and cyclic oligomers derived from formaldehyde.

Preferably, the reaction mixture comprises the formaldehyde source in an amount ranging from about 0.1 to about 60 wt-% or about 1 to less than about 30 wt.-%, more preferably from about 5 to about 15 wt-%, further preferably ranging from about 7 to about 13 wt-% and most preferred ranging from about 8 to about 12 wt-%, especially ranging from 30 to 60 wt.-% based on the total weight of the reaction mixture.

It has been found that especially good results in terms of conversion can be achieved when the weight ration of formaldehyde/water of the formaldehyde source is greater than 4, preferable greater than 10 most preferably greater than 20.

Typically, the reaction is carried out at a temperature higher than about 0° C., preferably ranging from about 30° C. to about 170° C., more preferably ranging from about 40° C. to about 140° C., further preferably from about 40° C. to about 120° C. and most preferably from about 50° C. to about 110° C.

The pressure during the reaction can generally be from about 10 millibars to about 20 bars, such as from about 0.5 bar to about 10 bar, such as from about 0.5 bar to about 2 bar.

A further advantage of the process of the present invention is that the cyclic acetals can easily be separated from the reaction mixture. The cyclic acetal, especially the trioxane can be separated from the reaction mixture by distillation in a high purity grade. Especially in case aprotic compounds (such as sulfolane) having a boiling point higher than about 20° C. above the boiling point of the cyclic acetals is used the formed cyclic acetals can simply be distilled off. In case sulfolane is used as the aprotic compound the formed trioxane can be distilled off without the formation of an azeotrope of sulfolane with trioxane. The process of the invention can be carried out batch wise or as a continuous process.

In a preferred embodiment the process is carried out as a continuous process wherein the formaldehyde source is continuously fed to the liquid medium comprising the catalyst and wherein the cyclic acetals, e.g. the trioxane, is continuously separated (isolated) by separation methods such as distillation.

The process of the invention leads to an extremely high conversion of the formaldehyde source to the desired cyclic acetals.

According to a preferred embodiment the final conversion of the formaldehyde source to the cyclic acetal is greater than 10%, based on initial formaldehyde source.

The final conversion refers to the conversion of the formaldehyde source into the cyclic acetals in the liquid system. The final conversion corresponds to the maximum conversion achieved in the liquid system.

The final conversion of the formaldehyde source to the cyclic acetals can be calculated by dividing the amount of cyclic acetals (expressed in wt.-%, based on the total weight of the reaction mixture) in the reaction mixture at the end of the reaction divided by the amount of formaldehyde source (expressed in wt.-%, based on the total weight of the reaction mixture) at the beginning of the reaction at t=0.

For example the final conversion of the formaldehyde source to trioxane can be calculated as:

Final conversion=(amount of trioxane in the reaction mixture expressed in weight-% at the end of the reaction)/(amount of formaldehyde source in the reaction mixture expressed in weight-% at $t=0$ [initial amount of formaldehyde source in the reaction mixture]).

According to a further preferred embodiment of the process of the invention the final conversion of the formaldehyde source into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

The process for producing cyclic acetals in accordance with the present disclosure can be conducted continuously or can be conducted in a batch-wise manner (discontinuous). Referring to FIG. 1, one embodiment of a continuous process for producing a cyclic acetal in accordance with the present disclosure is shown. The process illustrated in FIG. 1 is particularly well suited for converting anhydrous formaldehyde gas into a cyclic acetal such as trioxane. It should be understood, however, that the process in FIG. 1 may also be used to process any of the formaldehyde sources described above.

Referring to FIG. 1, the process includes an inlet stream 10 for feeding a formaldehyde source to a first fixed bed reactor 12. In one embodiment, the inlet 10 is for feeding a gaseous formaldehyde, or a gaseous/paraformaldehyde fluid stream to the reactor 12. In addition to the inlet stream 10, the process also includes aprotic compound stream 14 for feeding an aprotic compound to the reactor 12 in combination with the formaldehyde source. The aprotic compound fed to the reactor, for instance, may comprise liquid sulfolane. In one embodiment, for instance, a liquid aprotic compound is fed to the reactor that is not heated and is at a temperature of less than about 50° C., such as less than about 40° C., such as from about 15° C. to about 25° C.

The fixed bed reactor 12, in one embodiment, can contain a solid catalyst. The catalyst bed can be placed above, below, or in between inert materials, such as solid oxides, or a mixture of solid oxides. The inert materials may improve the radial distribution of the gas/liquid stream and avoid loss of catalyst. Use of the inert material, however, is optional.

In one embodiment, the fixed bed reactor 12 is operated as a continuous-liquid trickle bed reactor. For instance, the gas and the liquid velocity can be selected such that a trickle flow regime or a pulsating regime is achieved. Superficial liquid velocities can be between about 5 m/hr to about 20 m/hr, such as from about 15 m/hr to about 100 m/hr. The liquid-gas mass ratio at the reactor inlet can be between about 2 kg/kg to about 30 kg/kg, such as from about 5 kg/kg to about 10 kg/kg.

The temperature within the reactor 12 can be from about 30° C. to about 200° C., such as from about 80 C to about 120° C.

The pressure within the reactor 12 can generally be from about 0.15 bar to about 5 bar (absolute), such as from about 1 bar to about 2 bar.

Within the fixed bed reactor 12, the formaldehyde source is converted into a cyclic acetal. A gas/liquid stream 15 is produced that is then fed to a gas/liquid flash drum 18. Within the flash drum 18, a gas-liquid separation takes place. In addition to a flash drum, the process may also include an integrated gas-liquid calming zone within the reactor.

From the flash drum 18, a hot liquid outlet stream 22 is produced that is then fed to a heat exchanger 20. The heat exchanger 20 can remove the heat of dissolution and the heat of reaction. A vapor/unconverted formaldehyde stream 26 is also produced by the flash drum 18.

As shown in FIG. 1, in one embodiment, the hot liquid outlet stream 22, which contains the cyclic acetal can be split into a first liquid stream 28 and a second liquid steam 16. The second liquid stream 16 comprises a recycled liquid product stream that is fed back to the first fixed bed reactor 12. The liquid stream 28, on the other hand, is fed to a second fixed bed reactor 24. In addition, the vapor stream 26 is also fed to the second fixed bed reactor 24. The second fixed bed reactor 24 can operated similar to the first fixed bed reactor 12. The second fixed bed reactor is a "polishing" reactor that is designed to further increase conversion of the formaldehyde source into the cyclic acetal. Through the process shown in FIG. 1, for instance, formaldehyde conversion to the cyclic acetal can be greater than about 50%, such as greater than about 70%, such as greater than about 90%. In one embodiment, for instance, more than 95%, such as more than 98%, such as even more than 99% of the formaldehyde source may be converted into a cyclic acetal.

The second fixed bed reactor 24, produces a gas/liquid outlet stream 30 that is then fed to a second flash drum 32. The flash drum 32 produces an off gas stream 36 and a product stream 34. The product stream 34 contains the cyclic acetal, such as trioxane, the aprotic compound, water and formaldehyde. The product stream 34 can be fed to a distillation process for separating and removing the cyclic acetal. The aprotic compound can also be separated and fed back to the first fixed bed reactor 12.

Figure 2:
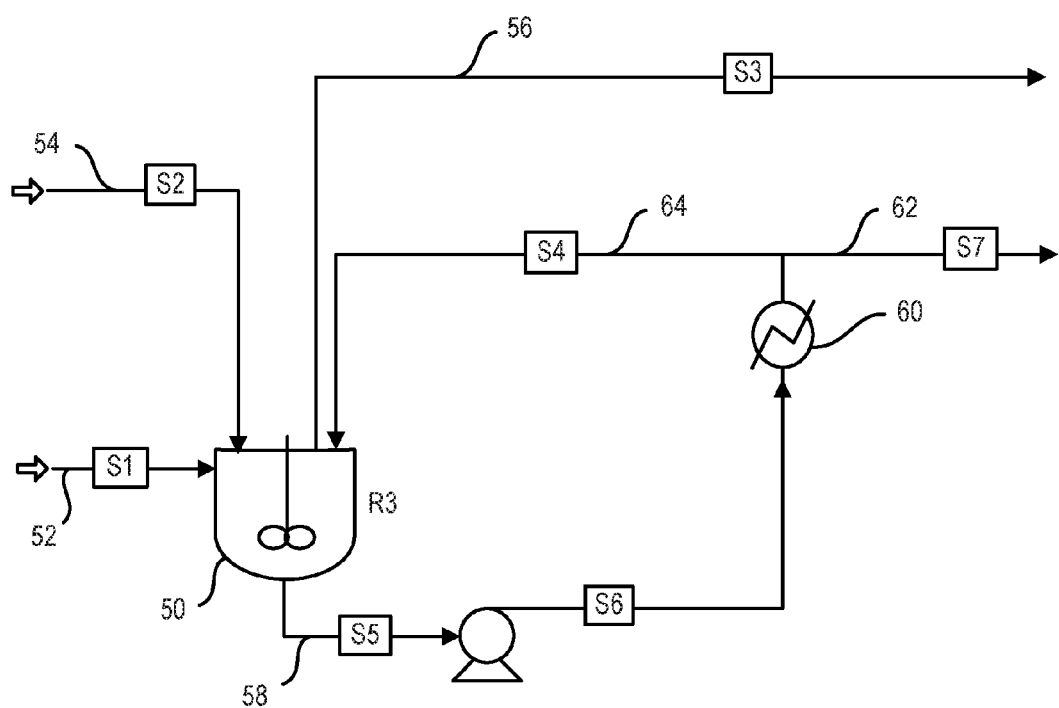
FIG. 2 is a schematic diagram of another embodiment of a process in accordance with the present disclosure.

Referring to FIG. 2, an alternative embodiment of a process in accordance with the present disclosure is shown. In the embodiment illustrated in FIG. 2, instead of a fixed bed reactor, the process includes a suspended reaction system. In particular, as shown in FIG. 2, the process includes a stirred tank reactor 50 that contains a suspended solid catalyst material. The catalyst concentration within the reactor can be less than about 75% by weight, such as less than about 50% by weight, such as less than about 50% by weight, such as less than about 3% by weight. The suspended catalyst is retained by means of filtration inside the reactor or by means of cross flow filtration outside the reactor. A formaldehyde source is fed to the reactor 50 through an input 52. The formaldehyde source, which may comprise formaldehyde gas, is dispersed within the reactor by means of stirring. The stirring power input to the system can be from about 0.01 kW/m$^3$, to about 20 kW/m$^3$, such as from about 0.1 kW/m$^3$, to about 3 kW/m$^3$.

In addition to a formaldehyde source, an aprotic compound is also fed to the reactor 50 through the aprotic compound feed line 54. The reactor 50 produces a liquid product stream 58 and an outgas stream 56. The reactor 50 can operate generally at the same pressures and temperatures as described above. The liquid product stream 58 containing a cyclic acetal is fed to a heat exchanger 60 for removing heat. In one embodiment, the liquid product stream 58 can be divided into a recycle stream 64 that is fed back to the reactor 50 and a product stream 62. The product stream 62 can contain primarily the liquid aprotic compound and the cyclic acetal such as trioxane. The liquid product stream 62 can be fed to a distillation process for removing and separating the trioxane. The aprotic compound can then be fed back to the reactor.

The present disclosure may be better understood with reference to the following example.

Cyclic acetals made according to the present disclosure can be used in numerous and diverse applications. In one embodiment, for instance, the cyclic acetals produced by the present disclosure may be used to produce an oxymethylene polymer.

The oxymethylene polymer production process may comprise any suitable process for producing oxymethylene homopolymers and/or copolymers. The polymer production process, for instance, may comprise an anionic polymerization process or a cationic polymerization process. The process for producing the oxymethylene polymer may comprise a heterogeneous process where the polymer precipitates in a liquid, may comprise a homogeneous process such as a bulk polymerization process that forms a molten polymer or may be a polymer process that includes both a heterogeneous phase and a homogeneous phase.

For the preparation of oxymethylene polymers, a monomer that forms —CH$_2$—O— units or a mixture of different monomers, are reacted in the presence of an initiator. Examples of monomers that form —CH$_2$O— units are formaldehyde or its cyclic oligomers, such as 1,3,5-trioxane (trioxane) or 1,3,5,7-tetraoxocane.

The oxymethylene polymers are generally unbranched linear polymers which generally contain at least 80 mol %, preferably at least 90 mol %, in particular at least 95 mol %, of oxymethylene units (—CH$_2$—O—). Alongside these, the oxymethylene polymers contain —(CH$_2$)x-O— units, where x can assume the values from 2 to 25. Small amounts of branching agents can be used if desired. Examples of branching agents used are alcohols whose functionality is three or higher, or their derivatives, preferably tri- to hexahydric alcohols or their derivatives. Preferred derivatives are formulas in which, respectively, two OH groups have been reacted with formaldehyde, other branching agents include monofunctional and/or polyfunctional glycidyl compounds, such as glycidyl ethers. The amount of branching agents is usually not more than 1% by weight, based on the total amount of monomer used for the preparation of the oxymethylene polymers, preferably not more than 0.3% by weight.

Oxymethylene polymers can also contain hydroxyalkylene end groups —O—$(CH_2)_x$—OH, alongside methoxy end groups, where x can assume the values from 2 to 25. These polymers can be prepared by carrying out the polymerization in the presence of diols of the general formula HO—$(CH_2)_x$—OH, where x can assume the values from 2 to 25. The polymerization in the presence of the diols leads, via chain transfer, to polymers having hydroxyalkylene end groups. The concentration of the diols in the reaction mixture depends on the percentage of the end groups intended to be present in the form of —O—$(CH_2)_x$—OH, and is from 10 ppm by weight to 2 percent by weight.

The molecular weights of these polymers, expressed via the volume melt index MVR, can be adjusted within a wide range. The polymers typically have repeat structural units of the formula —$(CH_2$—O—$)_n$—, where n indicates the average degree of polymerization (number average) and preferably varies in the range from 100 to 10 000, in particular from 500 to 4000.

Oxymethylene polymers can be prepared in which at least 80%, preferably at least 90%, particularly preferably at least 95%, of all of the end groups are alkyl ether groups, in particular methoxy or ethoxy groups.

Comonomers that may be used to produce oxymethylene copolymers including cyclic ethers or cyclic formals. Examples include, for instance, 1,3-dioxolane, diethylene glycol formal, 1,4-butanediol formal, ethylene oxide, propylene 1,2-oxide, butylene 1,2-oxide, butylene 1,3-oxide, 1,3 dioxane, 1,3,6-trioxocane, and the like. In general, one or more of the above comonomers may be present in an amount from about 0.1 to about 20 mol %, such as from about 0.2 to about 10 mol %, based on the amount of trioxane.

The molecular weight of the resultant homo- and copolymers can be adjusted via use of acetals of formaldehyde (chain transfer agents). These also lead to production of etherified end groups of the polymers, and a separate reaction with capping reagents can therefore be omitted. Chain transfer agents used are monomeric or oligomeric acetals of formaldehyde. Preferred chain transfer agents are compounds of the formula I

in which $R^1$ and $R^2$, independently of one another, are monovalent organic radicals, preferably alkyl radicals, such as butyl, propyl, ethyl, and in particular methyl, and q is a whole number from 1 to 50.

Particularly preferred chain transfer agents are compounds of the formula I, in which q=1, very particularly preferably methylal.

The amounts used of the chain transfer agents are usually up to 5000 ppm, preferably from 100 to 3000 ppm, based on the monomer (mixture).

The present disclosure may be better understood with reference to the following example.

Example 1

In this example, a strongly acidic ion exchange resin (Amberlyst 15®, wet form, from DOW CHEMICAL) was used as the catalyst.
Before use, the resin was conditioned to sulfolane (exchange of water in the pores of the resin by sulfolane).
9 g of commercial paraformaldehyde with a water content of ca. 4 wt-% were added to 91 g of sulfolane at 145° C. with stirring. As the paraformaldehyde dissolves the temperature decreases to 122° C. The clear solution was allowed to cool to 100° C. At that temperature 10 g of Amberlyst 15® was added. After 10 min at 100° C. the reaction mixture was allowed to cool to 50° C., and no precipitate formed, indicating the conversion of the paraformaldehyde to trioxane. The concentration of the trioxane in the reaction mixture is estimated to be above 6 wt-%.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:
1. A process for producing a cyclic acetal comprising:
   contacting a formaldehyde source with a liquid medium comprising a liquid aprotic compound in the presence of a heterogeneous catalyst, the heterogeneous catalyst comprising a solid catalyst, the aprotic compound having a boiling point of 140° C. or higher, determined at 1 bar; and
   at least partially converting the formaldehyde source into a cyclic acetal.
2. A process as defined in claim 1, wherein the heterogeneous catalyst comprises an add ion-exchange material.
3. A process as defined in claim 1, wherein the heterogeneous catalyst comprises a Lewis add or a Broensted add fixed on a solid support.
4. A process as defined in claim 3, wherein the solid support is an inorganic material.
5. A process as defined in claim 3, wherein the solid support is an organic material comprising a polymer.
6. A process as defined in claim 1, wherein the formaldehyde source comprises gaseous formaldehyde.
7. A process as defined in claim 1, wherein the formaldehyde source comprises a paraformaldehyde, polyoxymethylene homo- or compolymer, an aqueous formaldehyde solution, or mixtures thereof.
8. A process as defined in claim 1, wherein the formaldehyde source comprises a mixture of formaldehyde with trioxane.
9. A process as defined in claim 1, where in the heterogeneous catalyst comprises a Lewis add or Broensted add dissolved in an organic molten salt immobilized on a solid support.
10. A process as defined in claim 1, wherein the formaldehyde source is converted into the cyclic acetal at a temperature of from about 80° C. to about 120° C., and at a pressure from about 0.15 bar to about 5 bar.
11. A process for producing a cyclic acetal comprising:
   contacting a formaldehyde source with a liquid medium comprising a liquid aprotic compound in the presence of a heterogeneous catalyst, the heterogeneous catalyst comprising a solid catalyst; and
   at least partially converting the formaldehyde source into a cyclic acetal,
   wherein the heterogeneous catalyst is contained in a fixed bed and wherein the formaldehyde source and liquid medium flow through the fixed bed at a superficial liquid velocity of from about 5 m/hr to about 200 m/hr.
12. A process as defined in claim 11, wherein the formaldehyde source is converted into a cyclic acetal in a reactor that has an inlet into which the formaldehyde source and liquid medium is fed, and wherein the reactor has a liquid-gas mass ratio at the reactor inlet of from about 2 kg/kg to about 30 kg/kg.

13. A process as defined in claim 1, wherein the formaldehyde source is converted into the cyclic acetal in an agitated tank reactor, the heterogeneous catalyst being suspended within the tank reactor.

14. A process according to claim 1, wherein the aprotic compound is a polar aprotic compound.

15. A process according to claim 11, wherein the aprotic compound has a boiling point of 140° C. or higher, determined at 1 bar.

16. A process according to claim 1 wherein the aprotic compound has a relative static permittivity of more than 15, determined at 25° C.

17. A process according to claim 1 wherein higher than 50%, of the formaldehyde source is converted into one or more cyclic acetals during the reaction.

18. A process according to claim 1 wherein the aprotic compound comprises a sulfur-containing organic compound.

19. A process according to claim 1 wherein the aprotic compound is represented by formula (I):

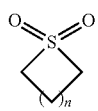
(I)

wherein
n is an integer ranging from 1 to 6, and
wherein the ring carbon atoms may optionally be substituted by one or more substituents, preferably selected from $C_1$-$C_8$-alkyl which may be branched or unbranched.

20. A process according to claim 1 wherein the aprotic compound is sulfolane.

21. A process according to claim 1 wherein the aprotic compound is represented by formula (II):

(II)

wherein $R^1$ and $R^2$ are independently selected from $C_1$-$C_8$-alkyl which may be branched or unbranched.

22. A process according to claim 1 wherein the aprotic compound is represented by formula (III):

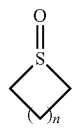
(III)

wherein
n is an integer ranging from 1 to 6, and
wherein the ring carbon atoms may optionally be substituted by one or more substituents, selected from $C_1$-$C_8$-alkyl which may be branched or unbranched; or
the aprotic compound is represented by formula (IV):

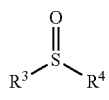
(IV)

wherein $R^3$ and $R^4$ are independently selected from $C_1$-$C_8$-alkyl which may be branched or unbranched.

23. A process according to claim 1, further comprising the step of separating the cyclic acetal from the liquid medium by distillation.

24. A process according to claim 1, further comprising the step of manufacturing polyoxymethylene from the cyclic acetal.

* * * * *

UNITED STATES PATENT AND TRADEMARK OFFICE
CERTIFICATE OF CORRECTION

PATENT NO. : 9,499,512 B2  
APPLICATION NO. : 14/359594  
DATED : November 22, 2016  
INVENTOR(S) : Michael Haubs et al.

Page 1 of 1

It is certified that error appears in the above-identified patent and that said Letters Patent is hereby corrected as shown below:

On the Title Page

Item (73) Name of Assignee should be changed to Celanese Sales Germany GmbH

Signed and Sealed this
Twenty-eighth Day of May, 2019

Andrei Iancu
*Director of the United States Patent and Trademark Office*